(12) United States Patent
Tanaka et al.

(10) Patent No.: US 7,312,239 B2
(45) Date of Patent: Dec. 25, 2007

(54) MEDICAMENT FOR PREVENTION AND/OR THERAPY OF ARTERIAL WALL DISORDER

(75) Inventors: Takayuki Tanaka, Niigata (JP); Tatsuhiko Mori, Takatsuki (JP)

(73) Assignee: Mitsubishi Pharma Corporation, Osaka (JP)

( * ) Notice: Subject to any disclaimer, the term of this patent is extended or adjusted under 35 U.S.C. 154(b) by 323 days.

(21) Appl. No.: 10/643,404

(22) Filed: Aug. 18, 2003

(65) Prior Publication Data

US 2004/0254234 A1 Dec. 16, 2004

(30) Foreign Application Priority Data

Sep. 4, 2002 (JP) .............................. 2002-258503

(51) Int. Cl.
*A61K 31/4152* (2006.01)
*A61K 31/381* (2006.01)
*A61K 31/341* (2006.01)

(52) U.S. Cl. .................... 514/406; 514/404; 514/443; 514/469; 514/471; 514/412; 514/405

(58) Field of Classification Search ................ 514/404, 514/165, 457, 573, 56, 406, 443, 469, 471, 514/412, 427, 405, 256, 414
See application file for complete search history.

(56) References Cited

U.S. PATENT DOCUMENTS 4,857,542 A * 8/1989 Nishi et al. .................. 514/404
RE35,801 E * 5/1998 Nishi et al. .................. 514/404

FOREIGN PATENT DOCUMENTS

| EP | 1386606 A1 * | 2/2004 |
|----|---|---|
| JP | 09052831 A * | 2/1997 |
| WO | WO 0224667 A1 * | 3/2002 |

* cited by examiner

*Primary Examiner*—Brian Kwon
(74) *Attorney, Agent, or Firm*—David G. Conlin; Dwight D. Kim; Edwards Angell Palmer & Dodge LLP

(57) ABSTRACT

An object of the present invention is to provide a medicament and method which is useful for prevention and/or therapy of arterial wall injury. According to the present invention, there is provided a method for prevention and/or therapy of arterial wall injury which comprises a step of administering the pyrazolone derivative represented by the following formula (I) or the physiologically acceptable salt thereof, or the hydrate or solvate thereof in a preventively or therapeutically effective amount to mammals including humans:

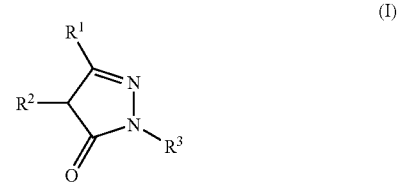

(I)

wherein $R^1$ represents a hydrogen atom, an aryl group, an alkyl group, or an alkoxycarbonylalkyl group; $R^2$ represents a hydrogen atom, an aryloxy group, an arylmercapto group, an alkyl group or a hydroxyalkyl group; or $R^1$ and $R^2$ are combined with each other to represent an alkylene group; and $R^3$ represents a hydrogen atom, an alkyl group, a cycloalkyl group, a hydroxyalkyl group, a benzyl group, a naphthyl group, a phenyl group, or a phenyl group substituted with 1 to 3 substituents selected from the group consisting of an alkyl group, an alkoxy group, a hydroxyalkyl group, an alkoxycarbonyl group, an alkylmercapto group, an alkylamino group, a dialkylamino group, a halogen atom, a trifluoromethyl group, a carboxyl group, a cyano group, a hydroxyl group, a nitro group, an amino group and an acetamide group.

5 Claims, 3 Drawing Sheets

Fig.3
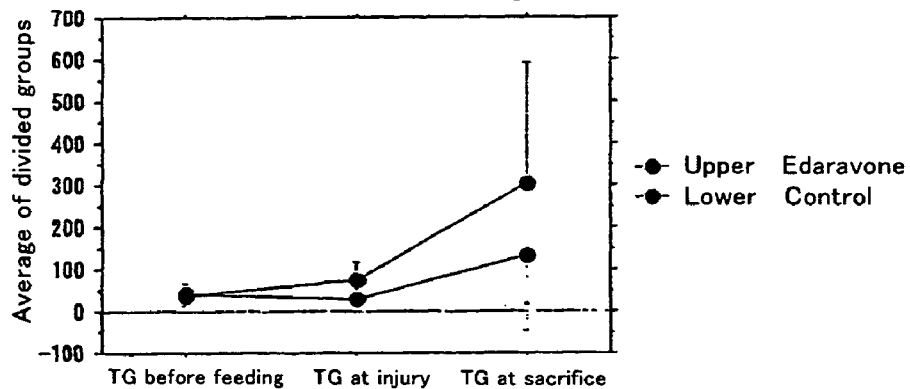
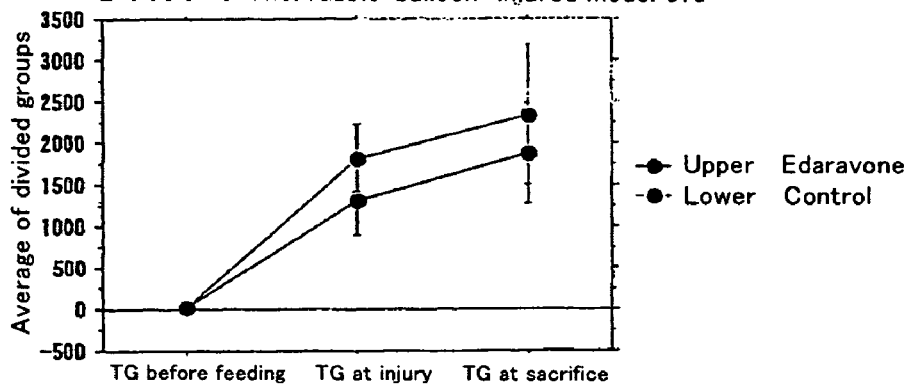
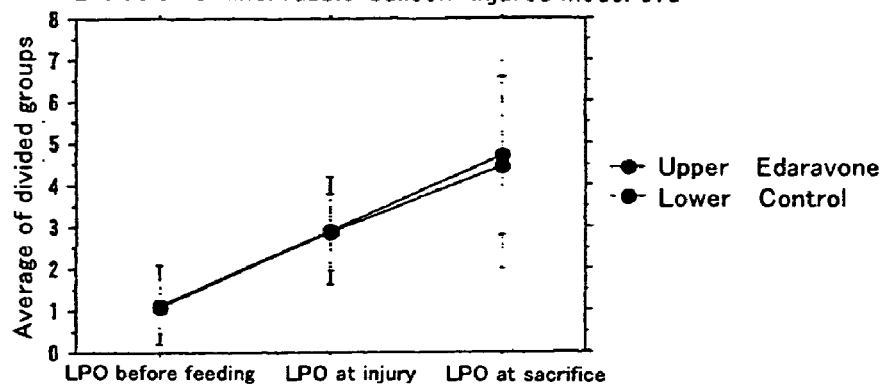

MEDICAMENT FOR PREVENTION AND/OR THERAPY OF ARTERIAL WALL DISORDER

TECHNICAL FIELD

The present invention relates to a medicament and method for prevention and/or therapy of arterial wall injury, which comprise as an active ingredient a pyrazolone derivative or a physiologically acceptable salt thereof, or a hydrate or solvate thereof.

BACKGROUND OF THE INVENTION

Coronary angioplasty is an intravascular surgery for dilating an occluded or stenosed lesion in the artery of the heart (coronary artery) by applying the catheterization. It is used for the therapy of ischemic heart diseases such as angina pectoris or myocardial infarction. Coronary angioplasty is called percutaneous transluminal coronary angioplasty (hereinafter abbreviated as PTCA) or percutaneous coronary intervention (hereinafter abbreviated as PCI) (hereinafter, the term "PTCA" is used in the present invention to include both PTCA and PCI.). Examples of the type of an apparatus used in the angioplasty may include a balloon (balloon catheter), reticulated metal (stent), a rapidly rotating olive-shaped drill (rotor plate), and DCA in which a cutter is pressed against arteriosclerotic tissues to incise them. Since PTCA is a treatment which mechanically dilates blood vessels, a fetal complication may be occasionally developed. Other than such a complication, "restenosis", wherein the dilated portion is narrowed again, is also problematic. It has been reported so far that various types of antioxidant substances suppress neointimal formation in animal models injured by use of a balloon (Gordon A. A., et al., Proc. Natl. Acad. Sci., USA, 89, 11312-11316, 1992).

Regarding a pyrazolone derivative which is represented by the following formula (I):

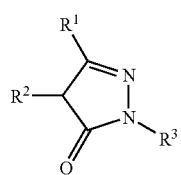

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl or $C_{1-3}$ hydroxyalkyl, or $R^1$ and $R^2$ are combined with each other to represent $C_{3-5}$ alkylene group, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, halogen atom, trifluoromethyl, carboxyl, cyano, hydroxyl group, nitro, amino and acetamide), examples of the known medical applications include cerebral function-normalizing action (JP Patent Publication (Kokoku) No. 5-31523 B (1993)), lipid peroxide production-suppressing action (JP Patent Publication (Kokoku) No. 5-35128, B (1993), anti-ulcer action (JP Patent Publication (Kokai) No. 3-215425 (1991)) and anti-hyperglycemic action (JP Patent Publication (Kokai) No. 3-215426 (1991)).

Among the compounds represented by the above formula (I), a pharmaceutical preparation containing 3-methyl-1-phenyl-2-pyrazolin-5-one as an active ingredient has been commercially available as a protective agent for the brain (under the general name "edaravone" and the commercial name "Radicut": produced and marketed by Mitsubishi Pharma Corporation) since June 2001. This "edaravone" has been reported to have high reactivity to active oxygen (Kawai, H., et al., J. Phamacol. Exp. Ther., 281(2), 921, 1997; and Wu, T W. et al., Life Sci, 67(19), 2387, 2000). As described above, edaravone is a free radical scavenger which prevents cell damage and the like by removing various free radicals including active oxygen. However, a study of whether or not edaravone is effective against arterial wall injury, has not been reported at all.

DISCLOSURE OF THE INVENTION

An object of the present invention is to provide a medicament and method which is useful for prevention and/or therapy of arterial wall injury.

As a result of various studies directed towards achieving the above-described objects, the present inventors have found that a pyrazolone derivative represented by the formula (I) or a physiologically acceptable salt thereof, or a hydrate or solvate thereof significantly suppresses neointimal formation in animal models injured by use of a balloon. The present invention has been completed based on the above findings.

According to the present invention, there is provided a method for prevention and/or therapy of arterial wall injury which comprises a step of administering the pyrazolone derivative represented by the following formula (I) or the physiologically acceptable salt thereof, or the hydrate or solvate thereof in a preventively or therapeutically effective amount to mammals including humans:

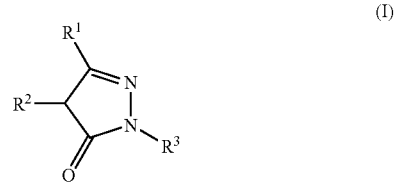

wherein $R^1$ represents a hydrogen atom, an aryl group, a $C_{1-5}$ alkyl group, or a $C_{3-6}$ (total carbon number) alkoxycarbonylalkyl group; $R^2$ represents a hydrogen atom, an aryloxy group, an arylmercapto group, a $C_{1-5}$ alkyl group or a $C_{1-3}$ hydroxyalkyl group; or $R^1$ and $R^2$ are combined with each other to represent $C_{3-5}$ alkylene group; and $R^3$ represents a hydrogen atom, a $C_{1-5}$ alkyl group, a $C_{1-5}$ cycloalkyl group, a $C_{1-3}$ hydroxyalkyl group, a benzyl group, a naphthyl group, a phenyl group, or a phenyl group substituted with the same or different 1 to 3 substituents selected from the group consisting of a $C_{1-5}$ alkyl group, a $C_{1-5}$ alkoxy group, a $C_{1-3}$ hydroxyalkyl group, a $C_{2-5}$ (total carbon number) alkoxycarbonyl group, a $C_{1-3}$ alkylmercapto group, a $C_{1-4}$ alkylamino group, a $C_{2-8}$ (total carbon number) dialkylamino group, a halogen atom, a trifluoromethyl group, a carboxyl group, a cyano group, a hydroxyl group, a nitro group, an amino group and an acetamide group.

According to a preferred embodiment of the present invention, the pyrazolone derivative represented by the formula (I) is 3-methyl-1-phenyl-2-pyrazolin-5-one or a physiologically acceptable salt thereof, or a hydrate or solvate thereof.

According to another aspect of the present invention, there is provided a medicament for prevention and/or therapy of arterial wall injury which comprises as an active ingredient the pyrazolone derivative represented by the formula (I) or the physiologically acceptable salt thereof, or the hydrate or solvate thereof. According to still another aspect of the present invention, there is provided the use of the pyrazolone derivative represented by the formula (I) or the physiologically acceptable salt thereof, or the hydrate or solvate thereof for producing the aforementioned medicament.

BRIEF DESCRIPTION OF THE DRAWINGS

FIG. 3 shows measurement results regarding total cholesterol (TC), triglyceride (TG) and lipid peroxide (LPO) in serum, which were measured, before the rabbits were fed with cholesterol food, when they were injured by use of a balloon, and when they were sacrificed.

BEST MODE FOR CARRYING OUT THE INVENTION

Figure 1:
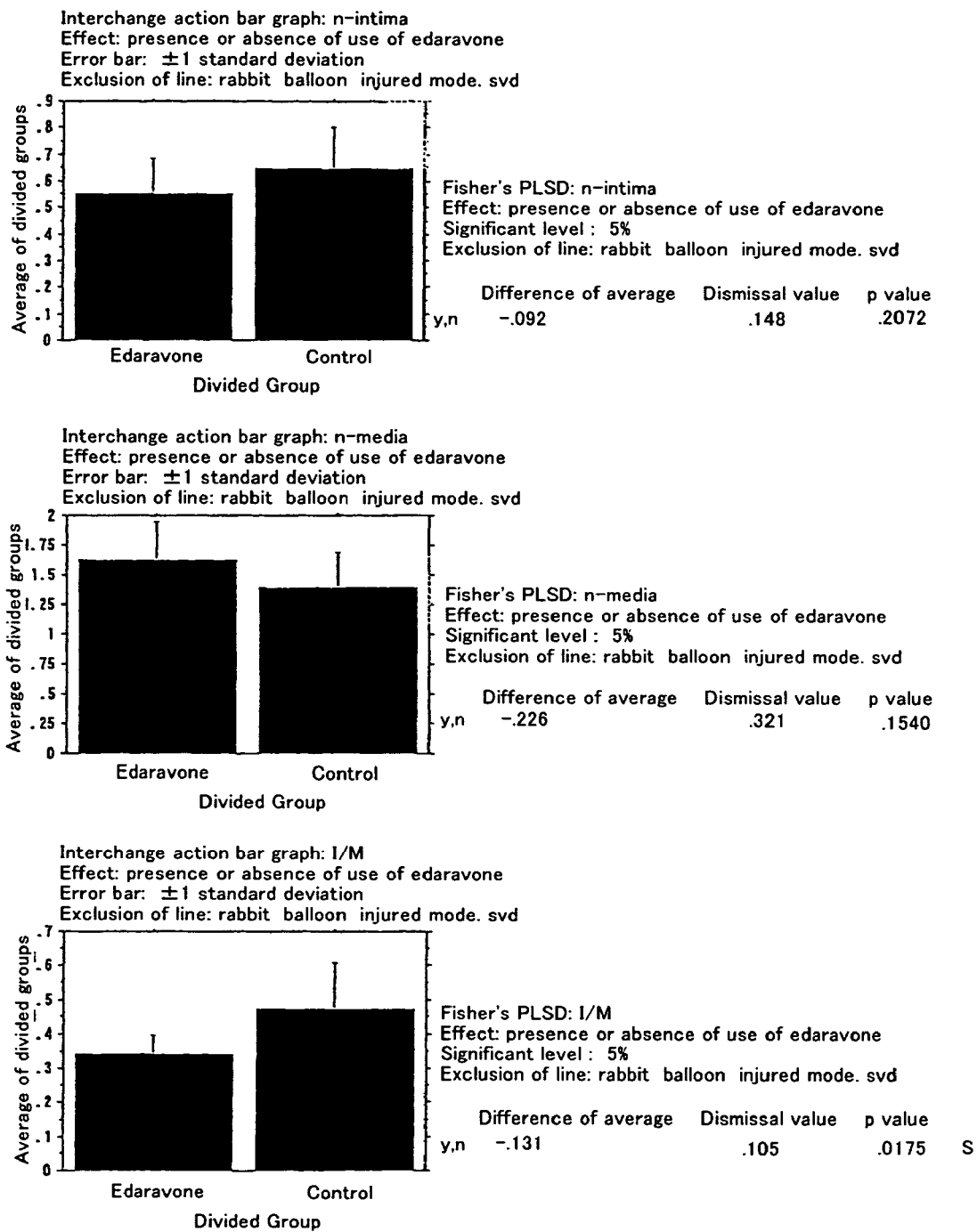
FIG. 1 shows the area of a new intima (n-intima) and that of a new media (n-media) in a cross-sectional sample from the abdominal aorta of rabbits injured by use of a balloon, and the ratio of these areas (I/M).

The medicament for prevention and/or therapy of arterial wall injury according to the present invention (hereinafter referred to as also "the medicament of the present invention") comprise the pyrazolone derivative represented by the formula (I) as defined in this specification or the physiologically acceptable salt thereof, or the hydrate or solvate thereof.

The compound represented by the formula (I) used in the present invention can have a structure represented by the following formula (I') or (I") due to tautomerism. One of the tautomers is shown in the formula (I) of this specification for convenience. The presence of the following tautomers is obvious to a person skilled in the art. As an active ingredient of the medicament of the present invention, the compound represented by the following formula (I') or (I") or a physiologically acceptable salt thereof, or a hydrate or solvate thereof may also be used.

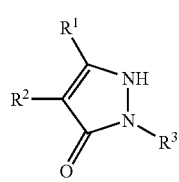

(I')

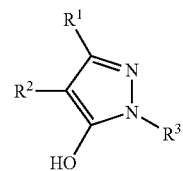

(I")

In the formula (I), the aryl group in the definition of $R^1$ may be either a monocyclic or polycyclic aryl group. Examples thereof include a phenyl group, a naphthyl group and the like, as well as a phenyl group substituted with a substituent such as an alkyl group (for example, a methyl group or a butyl group), an alkoxy group (for example, a methoxy group or a butoxy group), a halogen atom (for example, a chlorine atom) or a hydroxy group. The same applies for aryl portions in other substituents (e.g., an aryloxy group) having the aryl portions.

The $C_{1-5}$ alkyl group in the definition of $R^1$, $R^2$ and $R^3$ may be either linear- or branched chain. Examples thereof include a methyl group, an ethyl group, a propyl group, an isopropyl group, a butyl group, an isobutyl group, a sec-butyl group, a tert-butyl group, and a pentyl group. The same applies for alkyl portions in other substituents (alkoxycarbonylalkyl group) having the alkyl portions.

Examples of the $C_{3-6}$ (total carbon number) alkoxycarbonylalkyl group in the definition of $R^1$ include a methoxycarbonylmethyl group, an ethoxycarbonylmethyl group, a propoxycarbonylmethyl group, a methoxycarbonylethyl group and a methoxycarbonylpropyl group.

Examples of the aryloxy group in the definition of $R^2$ include a p-methylphenoxy group, a p-methoxyphenoxy group, a p-chlorophenoxy group and a p-hydroxyphenoxy group. Examples of the arylmercapto group include a phenylmercapto group, a p-methylphenylmercapto group, a p-methoxyphenylmercapto group, a p-chlorophenylmercapto group and a p-hydroxyphenylmercapto group.

Examples of the $C_{1-3}$ hydroxyalkyl group in the definition of $R^2$ and $R^3$ include a hydroxymethyl group, a 2-hydroxyethyl group and a 3-hydroxypropyl group. Examples of the $C_{5-7}$ cycloalkyl group in the definition of $R^3$ include a cyclopentyl group, a cyclohexyl group and a cycloheptyl group.

In the definition of $R^3$, examples of the $C_{1-5}$ alkoxy group that is the substituent of a phenyl group include a methoxy group, an ethoxy group, a propoxy group, an isopropoxy group, a butoxy group and a pentyloxy group; examples of the $C_{2-5}$ (total carbon number) alkoxycarbonyl group include a methoxycarbonyl group, an ethoxycarbonyl group, a propoxycarbonyl group and a butoxycarbonyl group; examples of the $C_{1-3}$ alkylmercapto group include a methylmercapto group, an ethylmercapto group and a propylmercapto group; examples of the $C_{1-4}$ alkylamino group include a methylamino group, an ethylamino group, a propylamino group and a butylamino group; and examples of the $C_{2-8}$ (total carbon number) dialkylamino group include a dimethylamino group, a diethylamino group, a dipropylamino group, and a dibutylamino group.

Examples of the compound (I) that is preferably used as an active ingredient of the medicament of the present invention include the following compounds.

3-methyl-1-phenyl-2-pyrazolin-5-one;
3-methyl-1-(2-methylphenyl)-2-pyrazolin-5-one;
3-methyl-1-(3-methylphenyl)-2-pyrazolin-5-one;

3-methyl-1-(4-methylphenyl)-2-pyrazolin-5-one;
3-methyl-1-(3,4-dimethylphenyl)-2-pyrazolin-5-one;
1-(4-ethylphenyl)-3-methyl-2-pyrazolin-5-one;
3-methyl-1-(4-propylphenyl)-2-pyrazolin-5-one;
1-(4-butylphenyl)-3-methyl-2-pyrazolin-5-one;
1-(3-trifluoromethylphenyl)-3-methyl-2-pyrazolin-5-one;
1-(4-trifluoromethylphenyl)-3-methyl-2-pyrazolin-5-one;
1-(2-methoxyphenyl)-3-methyl-2-pyrazolin-5-one;
1-(3-methoxyphenyl)-3-methyl-2-pyrazolin-5-one;
1-(4-methoxyphenyl)-3-methyl-2-pyrazolin-5-one;
1-(3,4-dimethoxyphenyl)-3-methyl-2-pyrazolin-5-one;
1-(4-ethoxyphenyl)-3-methyl-2-pyrazolin-5-one;
3-methyl-1-(4-propoxyphenyl)-2-pyrazolin-5-one;
1-(4-butoxyphenyl)-3-methyl-2-pyrazolin-5-one;
1-(2-chlorophenyl)-3-methyl-2-pyrazolin-5-one;
1-(3-chlorophenyl)-3-methyl-2-pyrazolin-5-one;
1-(4-chlorophenyl)-3-methyl-2-pyrazolin-5-one;
1-(3,4-dichlorophenyl)-3-methyl-2-pyrazolin-5-one;
1-(4-bromophenyl)-3-methyl-2-pyrazolin-5-one;
1-(4-fluorophenyl)-3-methyl-2-pyrazolin-5-one;
1-(3-chloro-4-methylphenyl)-3-methyl-2-pyrazolin-5-one;
1-(3-methylmercaptophenyl)-3-methyl-2-pyrazolin-5-one;
1-(4-methylmercaptophenyl)-3-methyl-2-pyrazolin-5-one;
4-(3-methyl-5-oxo-2-pyrazoline-1-yl) benzoic acid;
1-(4-ethoxycarbonylphenyl)-3-methyl-2-pyrazolin-5-one;
1-(4-nitrophenyl)-3-methyl-2-pyrazolin-5-one;
3-ethyl-1-phenyl-2-pyrazolin-5-one;
1-phenyl-3-propyl-2-pyrazolin-5-one;
1,3-diphenyl-2-pyrazolin-5-one;
3-phenyl-1-(p-tolyl)-2-pyrazolin-5-one;
1-(4-methoxyphenyl)-3-phenyl-2-pyrazolin-5-one;
1-(4-chlorophenyl)-3-phenyl-2-pyrazolin-5-one;
3,4-dimethyl-1-phenyl-2-pyrazolin-5-one;
4-isobutyl-3-methyl-1-phenyl-2-pyrazolin-5-one;
4-(2-hydroxyethyl)-3-methyl-1-phenyl-2-pyrazolin-5-one;
3-methyl-4-phenoxy-1-phenyl-2-pyrazolin-5-one;
3-methyl-4-phenylmercapto-1-phenyl-2-pyrazolin-5-one;
3,3',4,5,6,7-hexahydro-2-phenyl-2H-indazole-3-one;
3-(ethoxycarbonylmethyl)-1-phenyl-2-pyrazolin-5-one;
1-phenyl-2-pyrazolin-5-one;
3-methyl-2-pyrazolin-5-one;
1,3-dimethyl-2-pyrazolin-5-one;
1-ethyl-3-methyl-2-pyrazolin-5-one;
1-butyl-3-methyl-2-pyrazolin-5-one;
1-(2-hydroxyethyl)-3-methyl-2-pyrazolin-5-one;
1-cyclohexyl-3-methyl-2-pyrazolin-5-one;
1-benzyl-3-methyl-2-pyrazolin-5-one;
1-(α-naphthyl)-3-methyl-2-pyrazolin-5-one;
1-methyl-3-phenyl-2-pyrazolin-5-one;
3-methyl-1-(4-methylphenyl)-2-pyrazolin-5-one;
1-(4-butylphenyl)-3-methyl-2-pyrazolin-5-one;
1-(4-methoxyphenyl)-3-methyl-2-pyrazolin-5-one;
1-(4-butoxyphenyl)-3-methyl-2-pyrazolin-5-one;
1-(4-chlorophenyl)-3-methyl-2-pyrazolin-5-one;
1-(4-hydroxyphenyl)-3-methyl-2-pyrazolin-5-one;
1-(3,4-dihydroxyphenyl)-3-methyl-2-pyrazolin-5-one;
1-(2-hydroxyphenyl)-3-methyl-2-pyrazolin-5-one;
1-(3-hydroxyphenyl)-3-methyl-2-pyrazolin-5-one;
1-(4-hydroxyphenyl)-3-methyl-2-pyrazolin-5-one;
1-(3,4-hydroxyphenyl)-3-methyl-2-pyrazolin-5-one;
1-(4-hydroxyphenyl)-3-phenyl-2-pyrazolin-5-one;
1-(4-hydroxymethylphenyl)-3-methyl-2-pyrazolin-5-one;
1-(4-aminophenyl)-3-methyl-2-pyrazolin-5-one;
1-(4-methylaminophenyl)-3-methyl-2-pyrazolin-5-one;
1-(4-ethylaminophenyl)-3-methyl-2-pyrazolin-5-one;
1-(4-butylaminophenyl)-3-methyl-2-pyrazolin-5-one;
1-(4-dimethylaminophenyl)-3-methyl-2-pyrazolin-5-one;
1-(acetamidophenyl)-3-methyl-2-pyrazolin-5-one; and
1-(4-cyanophenyl)-3-methyl-2-pyrazolin-5-one:

As an active ingredient of the medicament of the present invention, a compound in a free form represented by the formula (I) as well as a physiologically acceptable salt thereof may also be used. Examples of the physiologically acceptable salt include a salt with mineral acid such as hydrochloric acid, sulfuric acid, hydrogen bromide salt or phosphoric acid; a salt with organic acid such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid or tartaric acid; a salt with alkaline metal such as sodium and potassium; a salt with alkaline earth metal such as magnesium or calcium; and a salt with amine such as ammonia, tris(hydroxymethyl)aminomethane, N,N-bis(hydroxyethyl)piperazine, 2-amino-2-methyl-1-propanol, ethanolamine, N-methyl glutamine or L-glutamine. Moreover, a salt with amino acid such as glycine may also be used As an active ingredient of the medicament of the present invention, a hydrate of a compound represented by the above formula (I) or a physiologically acceptable salt thereof, or a solvate of a compound represented by the above formula (I) or a physiologically acceptable salt thereof, may also be used. The type of an organic solvent used to form a solvate is not specifically limited. For example, methanol, ethanol, ether, dioxane or tetrahydrofuran can be exemplified. Furthermore, the compound represented by the above formula (I) may have 1 or more asymmetric carbons depending on the type of a substituent. A stereoisomer such as an optical isomer or a diastereoisomer may be present. As an active ingredient of the medicament of the present invention, a stereoisomer in a pure form, any mixture of stereoisomers, raceme or the like may also be used.

All the compounds represented by the formula (I) are known, and can be easily synthesized by a person skilled in the art using a method described in, for example, JP Patent Publication (Kokoku) No. 5-31523 B (1993).

The dose of the medicament of the present invention is not specifically limited. In general, the dose, as the weight of a compound (active ingredient) represented by the formula (I), is generally, in the case of oral administration, 0.1 to 1000 mg/kg body weight per day, preferably 0.5 to 50 mg/kg body weight per day, and in the case of parenteral administration, 0.01 to 100 mg/kg body weight per day and preferably 0.1 to 10 mg/kg body weight. Preferably, the above dose is administered once a day or administered on several (2 to 3) different occasions per day, and may be appropriately increased or decreased depending on age, pathological conditions or symptoms.

As the medicament of the present invention, the compound represented by the above formula (I) or the physiologically acceptable salt thereof, or the hydrate or solvate thereof may be administered as it is. In general, it is preferred that a pharmaceutical composition comprising the above substance which is an active ingredient, and a pharmacologically and pharmaceutically acceptable additive, is prepared and administered.

Examples of pharmacologically and pharmaceutically acceptable additives that can be used herein include excipients, disintegrating agents or disintegrating adjuvant agents, binders, lubricants, coating agents, dye, diluents, base, solubilizing agents or solubilizing adjuvant agents, isotonizing agents, pH regulators, stabilizers, propellants and adhesives.

For a pharmaceutical composition appropriate for oral administration, as additives, there can be used for example excipients such as glucose, lactose, D-mannitol, starch or crystalline cellulose; disintegrating agents or disintegrating adjuvant agents such as carboxymethylcellulose, starch or carboxymetylcellulose calcium; binders such as hydroxypropylcellulose, hydroxypropylmethylcellulose, polyvinylpyrrolidone or gelatine; lubricants such as magnesium stearate or talc; coating agents such as hydroxypropylmethylcellulose, saccharose, polyethylene glycol or titanium oxide; and bases such as petrolatum, liquid paraffin, polyethylene glycol, gelatine, kaolin, glycerin, purified water or hard fat.

For a pharmaceutical composition appropriate for injection or drip, there can be used additives, for example, solubilizing agents or solubilizing adjuvant agents such as distilled water for injection, physiological saline or propylene glycol that can constitute an aqueous injection or an injection that is dissolved when used; isotonizing agents such as glucose, sodium chloride, D-mannitol or glycerine; and pH regulators such as inorganic acid, organic acid, inorganic base and organic base.

The form of the medicament of the present invention is not specifically limited, and may be any of the various forms that can be applied by a person skilled in the art. As a medicament appropriate for oral administration, for example, tablets, powders, granules, hard gelatin capsule agents, suppositories or troches can be prepared by using solid pharmaceutical additives, and for example, syrups, emulsions or soft gelatin capsule agents can be prepared by using liquid pharmaceutical additives. Furthermore, as a medicament appropriate for parenteral administration, injections, drops, inhalants, suppositories, percutaneous absorbents, trans-mucosal absorbents or the like can be prepared. A protective agent for the brain (drops) comprising as an active ingredient a compound represented by the above formula (I) has already been clinically used (under the general name "edaravone" and the commercial name "Radicut": produced and marketed by Mitsubishi Pharma Corporation). This commercially available pharmaceutical preparation can be used as it is for the medicament of the present invention.

The medicament of the present invention is useful for arterial wall injury. This is to say, the medicament of the present invention has an action as a preventive agent for preventing arterial wall injury, and/or an action as a therapeutic agent for repairing the arterial wall injury to a normal condition.

In the present specification, the term "arterial wall injury" is used to mean injury caused by percutaneous transluminal angioplasty (PTA), where an artery occluded or stenosed by arteriosclerosis is dilated by using a catheter, and in particular it means injury caused by PTCA. The type of an artery on which such an angioplasty is performed is not particularly limited, and examples thereof may include any types of artery such as coronary artery, cerebral blood vessel, or peripheral artery. In addition, examples of the type of an angioplasty may include, but not limited to, balloon vasodilatation (dilating a blood vessel with a balloon), stent placement (inserting a metal tool into a blood vessel to dilate it), transcatheter endarterectomy (cutting away lesion in a blood vessel; arterectomy, rotoblater), laser angioplasty (passing laser to an occluded lesion), and a combined use thereof. Moreover, the above term "arterial wall injury" may further include injury caused by coronary-artery bypass graft (hereinafter abbreviated as CABG), which connects a vein graft (for example, vein cut out of the crus of a patient to be operated) to above and below an occluded portion in a coronary artery, so as to ensure a sufficient vascular flow to the heart muscle. Furthermore, the "arterial wall injury" means, for example, neointimal formation, the restenosis or reocclusion of vascular lumens, and decrease in elasticity and flexibility.

The administration route of the medicament of the present invention is not particularly limited, and the medicament can be administered orally or parenterally. For example, the medicament of the present invention can be orally administered for a preventive purpose before performing PTCA or CABG. Alternatively, it can be administered for a preventive purpose via a parenteral route such as an injection or drop, during, before or after performing PTCA or CABG. In addition, it can also be administered in the form of an intravenous or arterial injection to patients suffering from restenosis after undergoing PTCA or CABG for the purpose of preventing deterioration of the symptom or alleviating the symptom.

EXAMPLES

The present invention will be described more specifically by the following examples. The scope of the present invention is not limited by the following examples.

SYNTHETIC EXAMPLE

Synthesis of 3-methyl-1-phenyl-2-pyrazolin-5-on (Hereinafter Referred to as Edaravone)

13.0 g of ethyl acetoacetate and 10.8 g of phenylhydrazine were added in 50 ml of ethanol, followed by 3 hours of reflux and stirring. After the reaction solution was allowed to stand to cool, the precipitated crystal was collected by filtration, and then recrystalized with ethanol, thereby obtaining 11.3 g of the subject compound in the form of colorless crystals.

Yield: 67%

Melting point: 127.5 to 128.5° C.

Example 1

(1) Experiment Method

Japanese white rabbits were divided into two groups, an edaravone group (n=6) and a control group (n=6), and they were fed with 1% cholesterol food for 10 weeks. On the $8^{th}$ week, the rabbits of both groups were injured such that their abdominal aorta was damaged by use of a balloon. For the edaravone group, edaravone was administered every day (10 mg/kg, intravenous injection twice per day) from the day before the balloon injury. For the control group, a physiological salt solution was administered. On the $10^{th}$ week, the rabbits were sacrificed, and their abdominal aorta was excised. The ratio of a new intima to a new media (the ratio of the intimal area of a blood vessel section to the medial area thereof; I/M) was measured as follows. First, total 5 portions were cut out of the abdominal aorta into round slices each having a width of 5 mm, and HE-stained samples were prepared therefrom. A new intimal area and a new medial area were analyzed with computer software, and the mean value of the 5 portions was obtained, followed by calculation of I/M.

Moreover, total cholesterol (TC), triglyceride (TG) and lipid peroxide (LPO) in serum were measured, before the rabbits were fed with cholesterol food, when they were injured by use of a balloon, and when they were sacrificed.

(2) Experiment Results

1. Ratio of New Intima to New Media (I/M)

FIG. 1 shows the area of a new intima (n-intima) and that of a new media (n-media) in a cross-sectional sample from the abdominal aorta of rabbits injured by use of a balloon, and the ratio of these areas (I/M). The I/M of the edaravone group (0.344±0.055) was significantly (p=0.018) lower than that of the control group (0.475±0.136), and it can be said that neointimal formation was suppressed in the edaravone group rather than in the control group.

2. Relationship Between LPO (Lipid Peroxide) and the Ratio of a New Intima to a New Media (I/M)

Figure 2:
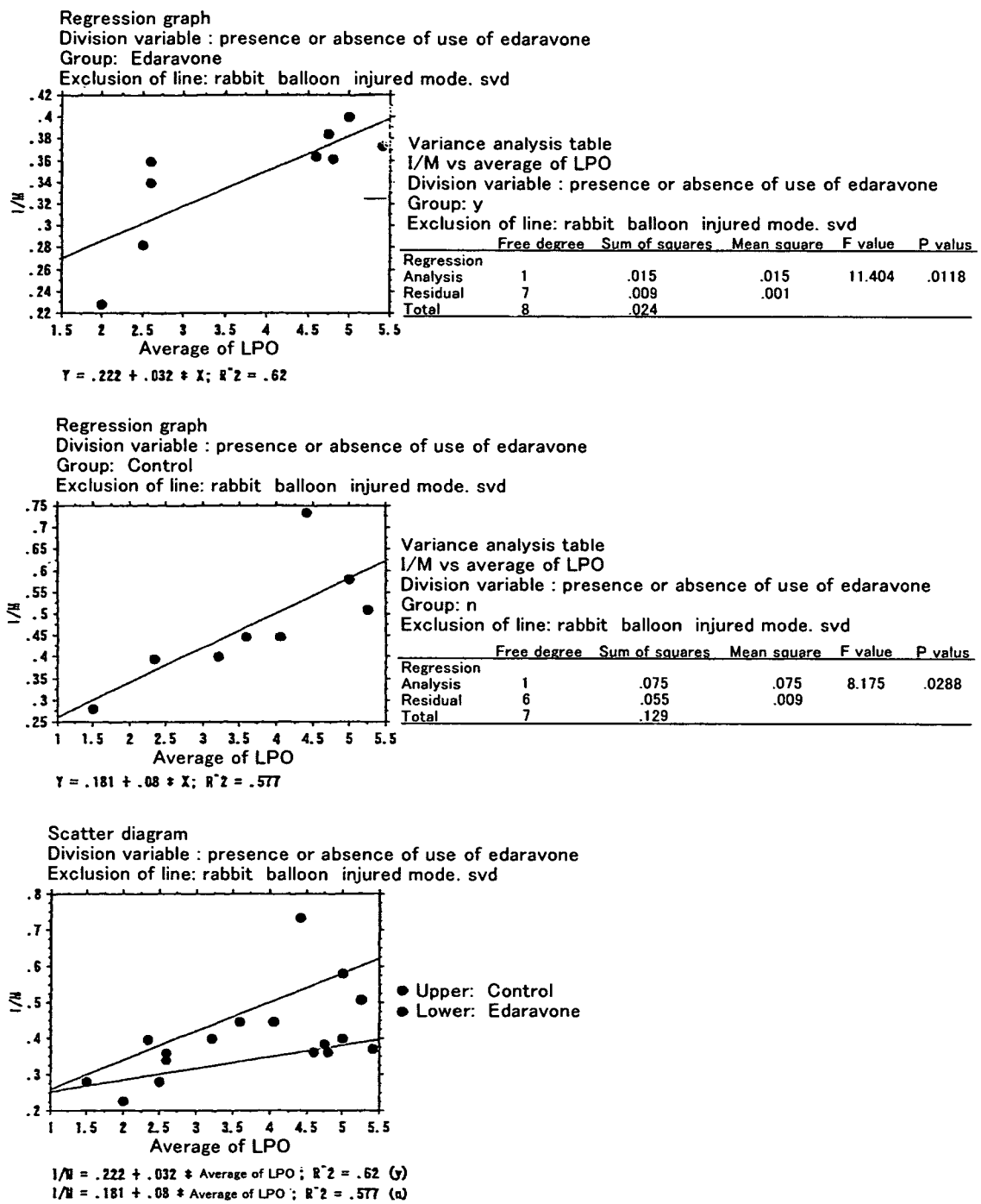
FIG. 2 shows a relationship between LPO (lipid peroxide) and the area ratio of a new intima to a new media (I/W) (the upper figure: an edaravone group; the central figure: a control group; and the lower figure: a view of overlaying the edaravone group on the control group).

FIG. 2 shows a relationship between LPO (lipid peroxide) and the area ratio of a new intima to a new media (I/M) (the upper figure: the edaravone group; the central figure: the control group; and the lower figure: a view of overlaying the edaravone group on the control group). In the control group, I/M had a significantly positive correlation with LPO (r=0.76, p=0.029). In the edaravone group also, I/M had such a positive correlation with LPO (r=0.79, p=0.012). A gradient obtained from a regression formula in the edaravone group was smaller than that in the control group. A difference in gradients from regression formulas in both groups suggests that the effect of edaravone for suppressing neointimal formation be achieved by a mechanism that is different from the suppression of oxidization by serum lipid.

3. Total Cholesterol (TC), Triglyceride (TG) and Lipid Peroxide (LPO) in Serum

TC, TG and LPO measured at each of the above time points were not significantly different between both groups. Thus, edaravone did not have a clear effect on a lipid system such as TC, TG or LPO (FIG. 3). Accordingly, it was suggested that edaravone can suppress neointimal formation although it is administered in such a small dose that has no effects on lipid peroxide in serum.

Example 2

(1) Experiment Method

Experiment (1)

11'-week-old female SD rats were divided into two groups, an ovary elimination group (OVX) and an ovary non-elimination group (INT). To the OVX group, edaravone (Ed) (30 mg/kg/day) (n=8) or vehicle (V) (n=7) was orally administered, and to the INT group (n=4), vehicle (V) was administered. The vascular endothelium of the right common carotid artery was injured by abrasion with a 2F balloon. The above drugs were administered for 3 days immediately after the above operation. On the $14^{th}$ day, the blood vessel was excised, and the ratio of a new intima to a new media (I/M) was calculated.

Experiment (2)

30-week-old male OLETF rats with type II diabetes were divided into two groups, an edaravone (Ed) administration group (n=4) and a vehicle (V) administration group (n=4). The above-described blood vessel injury was carried out on them. The above drugs were continuously administered from 3 days before the above operation to the $14^{th}$ day after the above operation. Thereafter, the ratio of a new intima to a new media (I/M) was calculated.

(2) Experiment Results

Experiment (1)

Significant neointimal formation was observed in the ovary elimination+vehicle administration group (OVX+V) rather than in the ovary non-elimination+vehicle administration group (INT+V) (that is, I/M: 1.36±0.12 vs. 0.75±0.06). In the ovary elimination+edaravone administration group (OVX+Ed), such neointimal formation was significantly suppressed (p<0.01) (I/M: 0.82±0.09).

Experiment (2)

Significant neointimal formation observed in the vehicle (V) administration group was significantly suppressed in the edaravone (Ed) administration group (p<0.01) (I/M: 1.12±0.15 vs. 0.55±0.02).

INDUSTRIAL APPLICABILITY

The medicament of the present invention has an action of suppressing neointimal formation in a model with an aorta injured by use of a balloon. Accordingly, it is useful as a medicament for prevention and/or therapy of restenosis or neointimal formation developed after PTCA or CABG.

The entire content of Japanese Patent Application No.2002-258503, which the present application claims a priority based on, is incorporated herein by reference as a part of disclosure of the present specification.

What is claimed is:

1. A method for therapy of arterial wall injury which is caused by coronary angioplasty or coronary-artery bypass graft (CABG), which comprises a step of administering 3-methyl-1-phenyl-2-pyrazolin-5-one or the physiologically acceptable salt thereof, or the hydrate or solvate thereof in a therapeutically effective amount to a mammal to treat the arterial wall injury.

2. The method according to claim 1 wherein the arterial wall injury is restenosis or neointimal formation after coronary angioplasty or coronary-artery bypass graft (CABG).

3. The method according to claim 1, claim 2, or claim 4 wherein the coronary angioplasty is percutaneous transluminal coronary angioplasty (PCTA) or percutaneous coronary intervention (PCI).

4. A method for therapy of neointimal formation, restenosis, or reocclusion of vascular lumens, which is caused by coronary angioplasty or coronary-artery bypass graft (CABG), which comprises a step of administering 3-methyl-1-phenyl-2-pyrazolin-5-one or the physiologically acceptable salt thereof, or the hydrate or solvate thereof in a therapeutically effective amount to a mammal to treat the neointimal formation, restenosis or reocculsion of vascular lumens.

5. The method according to claim 1 or claim 4, wherein the mammal is a human.

* * * * *